United States Patent [19]

Fuchs

[11] 4,045,473
[45] Aug. 30, 1977

[54] ALKOXYCARBONYLISOUREA ISOCYANATES

[75] Inventor: Julius Jakob Fuchs, Wilmington, Del.

[73] Assignee: E. I. Du Pont de Nemours and Company, Wilmington, Del.

[21] Appl. No.: 603,651

[22] Filed: Aug. 11, 1975

[51] Int. Cl.$^2$ .................. C07C 127/26; C07C 155/02; C07C 157/14
[52] U.S. Cl. .......................... 260/482 C; 260/239 A; 260/455 A; 260/465 D; 260/468 E; 260/470; 260/471 C; 260/479 C; 260/481 C
[58] Field of Search ............ 260/482 C, 481 C, 455 A

*Primary Examiner*—Lorraine A. Weinberger
*Assistant Examiner*—Michael Shippen

[57] ABSTRACT

Certain novel carbamates of the formulas:

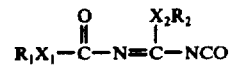

(I)

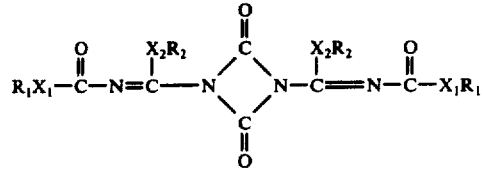

(II)

where $R_1$ is alkyl of 1-3 carbon atoms;
$R_2$ is alkyl of 1-4 carbon atoms; and
$X_1$ and $X_2$ are independently selected from oxygen and sulfur;

are useful intermediates to react with aromatic and aliphatic amines to yield herbicidal allophanimidates.

6 Claims, No Drawings

ALKOXYCARBONYLISOUREA ISOCYANATES

BACKGROUND OF THE INVENTION

The allophanimidates described in Belgian Pat. No. 796,011 granted Mar. 15, 1973 of the formula:

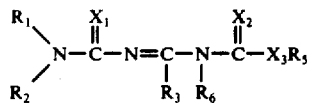

wherein
$X_1$, $X_2$, and $X_3$ are oxygen or sulfur;
$R_1$ is hydrogen or alkyl of 1 through 4 carbon atoms;
$R_2$ is alkyl of 1 through 6 carbon atoms, cycloalkyl of 3 through 8 carbon atoms, cycloalkylalkyl of 4 through 7 carbon atoms, alkenyl of 3 through 4 carbon atoms, alkynyl of 3 through 4 carbon atoms, benzyl, or

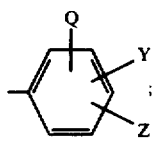

where
Y is hydrogen, halogen, alkyl of 1 through 4 carbon atoms, nitro, alkoxy of 1 through 4 carbon atoms, alkylthio of 1 through 4 carbon atoms, cyano, or trifluoromethyl; and
Z is hydrogen, halogen, methyl, ethyl, nitro, alkoxy of 1 through 4 carbon atoms, or alkylthio of 1 through 4 carbon atoms;
Q is hydrogen, halogen, or methyl;
$R_3$ is $SR_4$ or $OR_4$;
where $R_4$ is alkyl of 1 through 6 carbon atoms, cycloalkyl of 3 through 8 carbon atoms, alkenyl of 3 through 4 carbon atoms, alkynyl of 3 through 4 carbon atoms, benzyl or phenyl; and
$R_5$ is alkyl of 1 through 12 carbon atoms substituted with 0-3 chlorine atoms or 0-1 methoxy group, alkenyl of 3 through 4 carbon atoms, cycloalkyl of 5 through 8 carbon atoms, benzyl, or

where Y and Z are as previously defined;
$R_6$ is hydrogen or alkyl 1 through 3 carbon atoms; are useful as herbicides.

The existence of alternate processes for making these compounds allows the utilization of different starting materials and process equipment depending on availability and economics.

This invention provides such an alternative process for making many of the allophanimidates described in the Belgian patent.

SUMMARY OF THE INVENTION

This invention consists of novel compounds of the formulas:

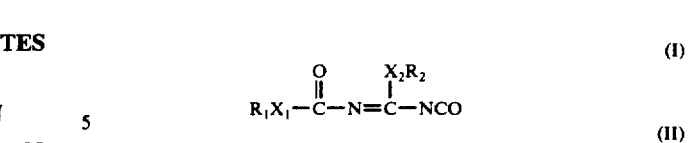
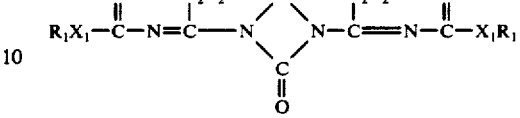

where
$R_1$ is alkyl of 1-3 carbon atoms;
$R_2$ is alkyl of 1-4 carbon atoms; and
$X_1$ and $X_2$ are independently selected from oxygen and sulfur.

These compounds are useful intermediates in a process for making certain of the herbicidal allophanimidates described in Belgian Pat. No. 796,011.

Preferred for economy of synthesis are those compounds of formulas I and II where
1. $R_1$ is methyl; or
2. $R_2$ is methyl; or
3. $X_1$ is oxygen; or
4. $X_2$ is oxygen.

Most preferred for economy of synthesis are the compounds where $R_1$ and $R_2$ are methyl and $X_1$ and $X_2$ are oxygen which are methyl N-[(isocyanato)(methoxy)methylene]carbamate and dimethyl N,N'-{[(2,4-dioxo-1,3-diazetidine)-1,3-diyl]-bis[(methoxy)methylidyne]}biscarbamate.

The isocyanates of formula I exist as monomeric entities in solution, but are isolated as dimers of formula II in the solid state.

DETAILED DESCRIPTION OF THE INVENTION

This invention relates to novel monomeric and dimeric isocyanates of the formulas

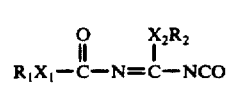

and

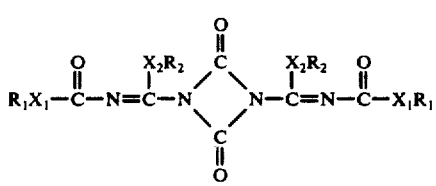

The preparation of the starting materials for synthesis of the invention compounds is known in the art. U.S. Pat. No. 3,855,219 discloses the synthesis of methyl

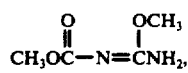

N-[(amino)(methoxy)methylene]carbamate, methyl N-[(amino)(methylthio)methylene]carbamate,

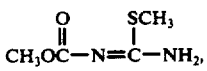

and of methyl N-[(amino)(methylthio)-methylene]thiolcarbamate,

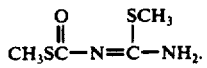

Similarly, the methyl N-[(amino)(methoxy)-methylene]thiolcarbamate,

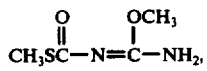

can be prepared along with the other needed carbamates of formula

In the process for making the novel isocyanates of this invention, the starting carbamates serve as HCl scavengers to produce an isocyanate in one step:

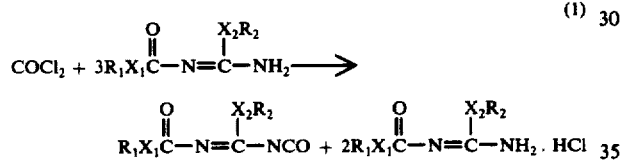
(1)

Even though equation (1) calls for a mole ratio of phosgene to carbamate equal to 1:3, it is preferred to utilize a mole ratio of at least 1:1 to avoid excessive formation of undesirable urea-type compounds according to the equation (2),

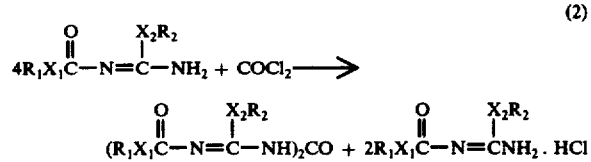
(2)

which is favored when mole ratios of less than 1:1 are employed. Higher mole ratios than 1:1 are possible.

The reaction is best performed in a solvent inert to phosgene and reaction products, and in which the starting carbamate and the product isocyanate are soluble. Such solvents are $CH_2Cl_2$, $CHCl_3$, $CCl_4$, benzene, toluene, xylene, ethyl acetate and acetonitrile. The carbamate is always added to the phosgene in one of the following ways:
a. neat carbamate to a solution of $COCl_2$;
b. carbamate in solution to neat $COCl_2$;
c. carbamate in solution to $COCl_2$ in solution.

The temperature of the $COCl_2$-carbamate reaction can be from $-20°$ to $60°$ C. It is, however, preferred to operate between $0°$ and $30°$ C because at the lower temperatures there are lesser amounts of urea-type products formed.

The reaction time depends on the reaction temperature, whereas the reaction is completed in 15–30 minutes at about 30° C., it will take from 30–60 minutes at 0° C to complete the reaction.

The carbamate-HCl salt produced as a byproduct precipitates, so it is preferred to use enough solvent to insure that the reaction mass at the end of the reaction can still be agitated. Up to 30% by weight of the reaction mass can consist of undissolved solids. These solids can be removed by filtration and dissolved in water to regenerate the free carbamate by neutralization of the HCl with NaOH. The carbamate can then be extracted with an inert organic solvent and recycled to the reaction with $COCl_2$. After the removal of the carbamate-HCl salt by filtration, the resulting filtrate contains the isocyanate together with the excess $COCl_2$. The $COCl_2$, being the lowest boiling component, can be removed and recovered by distillation and recycled to the reaction with the carbamate. The resulting distillation residue contains the monomeric isocyanate as indicated by the characteristic infrared absorption for the —NCO function at $\sim 4.5\mu$. This solution can then be used directly for the reaction with nucleophiles, such as

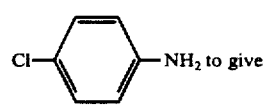

to give

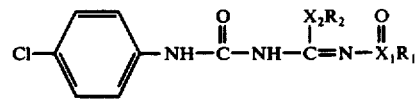

herbicidal allophanimidates.

If isolation of the isocyanate is desired, the solvent is removed, preferably under vacuum, leaving a solid which does not show the infrared absorption at $\sim 4.5\mu$. This solid is the dimeric isocyanate of formula II. As a solid, the isocyanate can be easily stored. When this solid is redissolved, the infrared absorption at $\sim 4.5\mu$ reappears, and this solution gives the same reaction product when reacted with aromatic and aliphatic amines as the original solution.

The original solution of the monomeric isocyanate as well as the isolated dimeric isocyanate, contain very small amounts of the urea-type compounds which do not interfere with subsequent reaction to obtain allophanimidates, and, if so desired, can be eliminated by recrystallizing the dimeric isocyanate from a suitable solvent. To determine the amount of urea-type compounds present, the dimeric isocyanate is isolated and decomposed with water, producing the original, water-soluble carbamate and $CO_2$. The urea-type compound is insoluble and can then be isolated by filtration and weighed.

The compounds of the invention are reacted with aromatic or aliphatic amines to yield allophanimidates of formula IV according to the following equation:

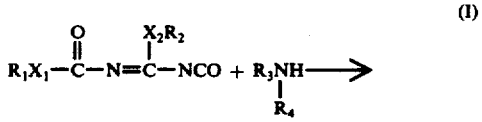
(I)

(IV)

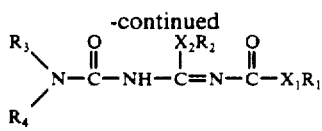

where
- $R_1$, $R_2$, $X_1$ and $X_2$ are defined as above;
- $R_3$ is hydrogen or alkyl of 1 through 4 carbon atoms;
- $R_4$ is alkyl of 1 through 6 carbon atoms, cycloalkyl of 3 through 8 carbon atoms, cycloalkylalkyl of 4 through 7 carbon atoms, alkenyl of 3 through 4 carbon atoms, benzyl, or

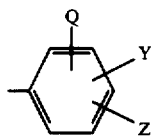

where
- Y is hydrogen, halogen, alkyl of 1 through 4 carbon atoms, nitro, alkoxy of 1 through 4 carbon atoms, alkylthio of 1 through 4 carbon atoms, cyano, or trifluoromethyl;
- Z is hydrogen, halogen, methyl, ethyl, nitro, alkoxy of 1 through 4 carbon atoms; and
- Q is hydrogen, halogen or methyl.

In the above equation, the isocyanate of formula I is reacted with 0.9 to 1.1 moles of the amine, $R_3R_4NH$, preferably 1.0 mole, at 0°–85° C., preferably 20°–50° C., in an inert organic solvent, such as halogen- or alkyl-substituted aromatics or chlorinated hydrocarbons, preferably methylene chloride, toluene or benzene. The mixture is stirred for 1.5 to 4 hours, depending on the other reaction conditions, and then evaporated to produce the allophanimidate in excellent yield and purity. The product can be further purified using conventional techniques.

EXAMPLE I

To a solution of 20 parts of phosgene in 335 parts methylene chloride is added at room temperature a solution of 26.4 parts methyl N-[(amino) (methoxy)methylene]carbamate in 67 parts methylene chloride. The temperature rises very fast to 39° C, while solids precipitate, and returns to room temperature within 0.5 hour. After stirring the reaction mass overnight, the solids are then removed by filtration. The solids are the hydrochloride salt of methyl N-[(amino)(methoxy)methylene]-carbamate. The filtrate, which contains methyl N-8 (isocyanato)(methoxy)methylene]carbamate can then be evaporated under vacuum to produce solids, which are recrystallized from a little methylene chloride to yield dimethyl N,N'-{[(2,4-dioxo-1,3-diazetidine)-1,3-diyl]-bis[(methoxy)methylidyne]}biscarbamate, m.p. 105°–107° C. The NMR spectrum of this biscarbamate solid shows two distinct peaks for —$OCH_3$.

To prepare an allophanimidate, 10 grams of cyclohexyl amine is gradually added, while maintaining the temperature below 30° C, to a solution of 15.8 grams of the solid biscarbamate dissolved in 100 ml of $CH_2Cl_2$; agitation is continued for 0.5 hour. After filtration through Celite, the filtrate is evaporated to give 27.2 grams of an oil, which, after trituration with petroleum ether, produced solid methyl N-methoxycarbonyl-4-cyclohexylallophanimidate, m.p. 79° –80.5° C.

EXAMPLE II

A series of experiments were run in which 39.6 parts of methyl N-[(amino)(methoxy)methylene]-carbamate were added to a solution of various parts of phosgene in 267 parts of methylene chloride at 0° C. After holding at 0° C for 0.5 hour, the precipitated solids were filtered off, the filtrate evaporated to dryness, and the resulting solids decomposed with water. After the $CO_2$-evolution had ceased, the undissolved solids were isolated by filtration, dried and weighed. These experiments give an indication of how the mole ratio of $COCl_2$/carbamate infuences the yield of the isocyanate, i.e., the yield loss to the coupled urea-type compounds.

| Moles $COCl_2$ to Carbamate | Wt. of Solids Filtered | Wt. of $CH_2Cl_2$ Residue | Wt. of $H_2O$ insol. mat. | % Yield loss to coupled prod. |
|---|---|---|---|---|
| .33 | 32.1 | 16.5 | 3.2 | 20 |
| .67 | 33.0 | 15.8 | 1.6 | 10 |
| 1.00 | 34.2 | 15.7 | 0.9 | 6 |
| 1.33 | 33.8 | 15.6 | 0.8 | 6 |
| 2.00 | 33.9 | 15.0 | 0.8 | 6 |
| 2.67 | 33.6 | 15.5 | 0.8 | 6 |

These experiments indicate that the minimum yield loss to urea-type compound is obtained when the mole ratio of $COCl_2$/carbamate is approximately 1:1 or greater.

EXAMPLE III

A solution of 110.5 parts of O-methylisourea hydrochloride in 475 parts of water is adjusted with 8.9 parts of 50% NaOH solution to pH 6. After raising the pH to 9, 114.5 parts of methyl chloroformate is added, while maintaining the pH at 9 by the simultaneous addition of 175.3 parts of 50% NaOH solution. The resulting reaction mass is then extracted 5 times with 134 parts methylene chloride, and the combined extracts are then dried by removing the dissolved water by azeotropic distillation. The resulting methylene chloride solution shows by gas chromatographic analysis the presence of 121.0 parts (92.25 yield) of methyl N-[(amino) (methoxy)methylene]carbamate. One-half of the above methylene chloride solution is gradually added to 45 parts of neat phosgene at 0° C within 10 minutes. Initially, gummy solids are formed, which gradually dissolve, as a white crystalline solid precipitates. After holding the temperature to 0° C for 30 minutes, 51.7 parts of solids are isolated by filtration. The filtrate is then evaporated to produce 23.5 parts of residue, which is almost completely soluble in water, and represents (based on equation (I) and the starting O-methylisourea hydrochloride) a 89.3% yield of crude dimethyl N,N'-{[(2,4-dioxo-1,3-diazetidine)-1,3-diyl]-bis[(methoxy)methylidyne]}biscarbamate.

To the other half of the methylene chloride solution obtained above is added a solution of 12.8 parts of p-chloroaniline in 67 parts of methylene chloride. The temperature is allowed to rise during the addition. When it has returned to 25° C, the reaction mass is cooled to 0° C, and the precipitated solids isolated by filtration to yield methyl N-methylcarbamoyl-4-(p-chlorophenyl)allophanimidate, m.p. 169°–171° C.

EXAMPLE IV

Substituting the following carbamates and thiolcarbamates for the methyl N-[(amino)(methoxy) methylene]-carbamate of Example I, the following monomeric and dimeric isocyanates can be produced.

| Starting Carbamate | Isocyanate Produced |
|---|---|
| Ethyl N-[(amino)(ethylthio)methylene]carbamate | Monomer: Ethyl N-[(isocyanato)(ethylthio)methylene-]carbamate<br>Dimer: Diethyl N,N'-{[2,4-dioxo-1,3-diazetidine)-1,3-diyl]-bis[(ethylthio)methylidyne-]}biscarbamate |
| Isopropyl N-[(amino)(propylthio)methylene]-carbamate | Monomer: Isopropyl N-[(isocyanato)(propylthio)methylene]carbamate<br>Dimer: Diisopropyl N,N'-{[(2,4-dioxo-1,3-diazitidine)-1,3-diyl]-bis[(propylthio)methylidyne]}biscarbamate |
| Methyl N-[(amino)(sec-butylthio)methylene]-carbamate | Monomer: Methyl N-[(isocyanato)(sec-butylthio)methylene]carbamate<br>Dimer: Dimethyl N,N'-{[(2,4-dioxo-1,3-diazetidine)-1,3-diyl]-bis[(sec-butylthio)methylidyne]}biscarbamate |
| Methyl N-[(amino)(methoxy)methylene]thiolcarbamate | Monomer: Methyl N-[(isocyanato)(methoxy)methylene]thiocarbamate. |
| | Dimer: Dimethyl N,N'-{[(2,4-dioxo-1,3-diazetidine)-1,3-diyl]-bis-[(methoxy)-methylidyne]}bisthiolcarbamate |

We claim:

1. A compound in solution in an inert organic solvent, which compound has the formula:

$$R_1X_1-\overset{O}{\underset{\|}{C}}-N=\overset{X_2R_2}{\underset{|}{C}}-NCO$$

wherein
$R_1$ is alkyl of 1–3 carbon atoms;
$R_2$ is alkyl of 1–4 carbon atoms; and
$X_1$ and $X_2$ are independently selected from oxygen and sulfur.

2. A compound of claim 1 wherein $R_1$ is methyl.
3. A compound of claim 1 wherein $R_2$ is methyl.
4. A compound of claim 1 wherein $X_1$ is oxygen.
5. A compound of claim 1 wherein $X_2$ is oxygen.
6. The compound of claim 1 where $R_1$ and $R_2$ are methyl and $X_1$ and $X_2$ are oxygen.

* * * * *